(12) United States Patent
Herbst et al.

(10) Patent No.: US 11,060,077 B2
(45) Date of Patent: Jul. 13, 2021

(54) LIPASES FOR USE IN WASHING AND CLEANING AGENTS

(71) Applicant: Henkel AG & Co. KGaA, Duesseldorf (DE)

(72) Inventors: Daniela Herbst, Duesseldorf (DE); Timothy O'Connell, Landsberg am Lech (DE); Nina Mussmann, Willich (DE); Renée Charlott Eichstaedt, Cologne (DE); Claudia Lindner, Solingen (DE); Georgette Koerfer, Stolberg (DE); Mehdi Davari Dolatabadi, Aachen (DE); Ljubica Vojcic, Aachen (DE); Ulrich Schwaneberg, Kelmis-Hergenrath (BE)

(73) Assignee: Henkel AG & Co. KGaA, Duesseldorf (DE)

( * ) Notice: Subject to any disclaimer, the term of this patent is extended or adjusted under 35 U.S.C. 154(b) by 246 days.

(21) Appl. No.: 16/087,595

(22) PCT Filed: Mar. 9, 2017

(86) PCT No.: PCT/EP2017/055500
§ 371 (c)(1),
(2) Date: Sep. 21, 2018

(87) PCT Pub. No.: WO2017/162440
PCT Pub. Date: Sep. 28, 2017

(65) Prior Publication Data
US 2020/0291367 A1    Sep. 17, 2020

(30) Foreign Application Priority Data

Mar. 23, 2016   (DE) .................. 102016204813.9

(51) Int. Cl.
*C12N 9/20* (2006.01)
*C11D 3/00* (2006.01)
*C11D 3/386* (2006.01)
*C11D 11/00* (2006.01)

(52) U.S. Cl.
CPC .............. *C12N 9/20* (2013.01); *C11D 3/0068* (2013.01); *C11D 3/38627* (2013.01); *C11D 11/0017* (2013.01); *C12Y 301/01003* (2013.01)

(58) Field of Classification Search
None
See application file for complete search history.

(56) References Cited

U.S. PATENT DOCUMENTS

| 2007/0179074 | A1 | 8/2007 | Souter et al. |
| 2020/0002691 | A1* | 1/2020 | Mussmann .............. C12N 9/20 |

FOREIGN PATENT DOCUMENTS

| WO | 2006084470 A2 | 8/2006 |
| WO | 2007087244 A2 | 8/2007 |
| WO | 2007087503 A1 | 8/2007 |

OTHER PUBLICATIONS

EPO, International Search Report and Written Opinion issued in International Application No. PCT/EP2017/055500, dated May 31, 2017.

* cited by examiner

*Primary Examiner* — Iqbal H Chowdhury
(74) *Attorney, Agent, or Firm* — Lorenz & Kopf, LLP

(57) ABSTRACT

The invention is used in the field of enzyme technology. The invention relates to lipases and to the production thereof, the amino acid sequence of which has been modified in particular with regard to the use thereof in detergents and cleaning agents, all sufficiently similar lipases having a corresponding modification and nucleic acids coding for them. The invention further relates to methods and uses of said lipases and to agents containing them, in particular detergents and cleaning agents.

7 Claims, No Drawings
Specification includes a Sequence Listing.

US 11,060,077 B2

SEQUENCE LISTING

<160> NUMBER OF SEQ ID NOS: 5

<210> SEQ ID NO 1

-continued

```
<211> LENGTH: 269
<212> TYPE: PRT
<213> ORGANISM: Thermomyces lanuginosus

<400> SEQUENCE: 1

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 2
<211> LENGTH: 269
<212> TYPE: PRT
<213> ORGANISM: Artificial
<220> FEATURE:
<223> OTHER INFORMATION: Optimized variant of SEQ ID NO:1

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60
```

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Arg Arg Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 3
<211> LENGTH: 269
<212> TYPE: PRT
<213> ORGANISM: Artificial
<220> FEATURE:
<223> OTHER INFORMATION: Optimized variant of SEQ ID NO:1

<400> SEQUENCE: 3

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

```
Gly Asn Gly Tyr Asp Ile Asp Val Phe Ser Tyr Gly Ala Pro Arg Val
            165                 170                 175

Gly Asn Arg Ala Phe Ala Glu Phe Leu Thr Val Gln Thr Gly Gly Thr
        180                 185                 190

Leu Tyr Arg Ile Thr His Thr Asn Asp Ile Val Pro Arg Leu Pro Asn
        195                 200                 205

Arg Glu Phe Gly Tyr Ser His Ser Ser Pro Glu Tyr Trp Ile Lys Ser
210                 215                 220

Gly Thr Leu Val Pro Val Arg Arg Asp Ile Val Lys Ile Glu Gly
225                 230                 235                 240

Ile Asp Ala Thr Gly Gly Asn Asn Gln Pro Asn Ile Pro Asp Ile Pro
            245                 250                 255

Ala His Leu Trp Tyr Phe Gly Leu Ile Gly Thr Cys Leu
            260                 265

<210> SEQ ID NO 4
<211> LENGTH: 269
<212> TYPE: PRT
<213> ORGANISM: Artificial
<220> FEATURE:
<223> OTHER INFORMATION: Optimized variant of SEQ ID NO:1

<400> SEQUENCE: 4

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Asn Gly Tyr Ser His Ser Ser Pro Glu Tyr Trp Ile Lys Ser
    210                 215                 220

Gly Thr Leu Val Pro Val Arg Arg Asp Ile Val Lys Ile Glu Gly
225                 230                 235                 240

Ile Asp Ala Thr Gly Gly Asn Asn Gln Pro Asn Ile Pro Asp Ile Pro
                245                 250                 255
```

```
Ala His Leu Trp Tyr Phe Gly Leu Ile Gly Thr Cys Leu
        260                 265
```

<210> SEQ ID NO 5
<211> LENGTH: 269
<212> TYPE: PRT
<213> ORGANISM: Artificial
<220> FEATURE:
<223> OTHER INFORMATION: Optimized variant of SEQ ID NO:1

<400> SEQUENCE: 5

```
Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Arg Arg Asp Ile Val Lys Ile Glu Gly
225                 230                 235                 240

Ile Asp Ala Thr Gly Gly Asn Asn Gln Pro Asn Ile Asn Asp Ile Pro
                245                 250                 255

Ala His Leu Trp Tyr Phe Gly Leu Ile Gly Thr Cys Leu
        260                 265
```

LIPASES FOR USE IN WASHING AND CLEANING AGENTS

CROSS-REFERENCE TO RELATED APPLICATION

This application is a U.S. National-Stage entry under 35 U.S.C. § 371 based on International Application No. PCT/EP2017/055500, filed Mar. 9, 2017, which was published under PCT Article 21(2) and which claims priority to German patent application no. 10 2016 204 813.9, filed Mar. 23, 2016, which are all hereby incorporated in their entirety by reference.

TECHNICAL FIELD

The present disclosure lies in the field of enzyme technology. The present disclosure relates in particular to lipases of which the amino-acid sequence has been altered, in particular with respect to use in washing and cleaning agents, to the preparation of said lipases, all reasonably similar lipases having a corresponding alteration and nucleic acids which code for said lipases. The present disclosure further relates to methods and uses of said lipases, and to agents, in particular washing and cleaning agents, which contain said lipases.

Lipases are among the industrially most significant enzymes of all. The use of lipases for washing and cleaning agents is industrially established and lipases are contained in virtually all modern, high-performance washing and cleaning agents. A lipase is an enzyme which catalyzes the hydrolysis of ester bonds in lipid substrates, in particular in fats and oils. Lipases are therefore a group of esterases. Lipases are generally versatile enzymes which accept a plurality of substrates, for example aliphatic, alicyclic, bicyclic and aromatic esters, thioesters and activated amines. Lipases are effective against fatty residues in laundry and catalyze the hydrolysis (lipolysis) of said fatty residues. Lipases which have wide substrate spectra are used in particular where inhomogeneous raw materials or substrate mixtures have to be reacted, for example in washing and cleaning agents, since stains may consist of differently structured fats and oils. The lipases used in washing or cleaning agents known in the prior art are usually of microbial origin and generally come from bacteria or fungi, for example from the genera *Thermomyces, Bacillus, Pseudomonas, Acinetobacter, Micrococcus, Humicola, Trichoderma* or *Trichosporon*. Lipases are usually produced, according to biotechnological methods that are known per se, from suitable microorganisms, for example from transgenic hosts of the genus *Bacillus* or from filamentous fungi. German patent application DE 102012224038 A1 and international patent application WO 2014/152674 disclose, for example, a lipase from *Thermomyces lanuginosus* (SEQ ID NO:2) that is provided for washing and cleaning agents. In general, only selected lipases are suitable for use in liquid surfactant preparations. Many lipases do not demonstrate sufficient catalytic performance or stability in preparations of this kind. However, using lipases produces an unpleasant odor on the washed objects, in particular textiles, after the washing process, since the lipases are absorbed by the textiles and continue to hydrolyze fatty acid esters to form fatty acids having a low molecular weight. These low-molecular-weight fatty acids are then noticed because of their unpleasant odor. The intensity of the odor can vary based on the condition of the textile. It is therefore desirable to find a lipase that demonstrates a sufficient washing performance and simultaneously causes minimal odor emissions for any kind of textile.

The lipases known from the prior art therefore produce odor emissions on washed textiles. In particular, these lipases are also not optimized to minimize their odor emission on various textiles.

BRIEF SUMMARY

This disclosure provides a lipase having an amino-acid sequence which is at least about 70% identical to the amino-acid sequence shown in SEQ ID NO:1 over the entire length thereof, and having at least one amino-acid substitution at at least one of the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, in each case based on the numbering according to SEQ ID NO:1.

This disclosure also provides a lipase obtained from a starting lipase acting as a starting molecule through one or more conservative amino-acid substitutions, the lipase having at least one amino-acid substitution at at least one of the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, e.g. 208, 211, or 253, in each case based on the numbering according to SEQ ID NO:1; and/or obtained from a starting lipase acting as a starting molecule through fragmentation, deletion, insertion, or substitution mutagenesis and has an amino-acid sequence which matches that of the starting molecule over a length of at least about 190, 200, 210, 220, 230, 240, 250, 260, or 269 interconnected amino acids, the lipase having at least one amino-acid substitution at at least one of the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, e.g. 208, 211, or 253, in each case based on the numbering according to SEQ ID NO:1.

This disclosure further provides a method for preparing a lipase, comprising substituting at least one amino acid at at least one of the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, e.g. 208, 211, or 253, in each case based on the numbering according to SEQ ID NO:1, in a starting lipase of which the sequence is at least about 70% identical to the amino-acid sequence shown in SEQ ID NO:1 over the entire length thereof, such that the lipase comprises an amino-acid substitution at least one of the positions. e.g. P208N, F211N, and P253N.

This disclosure also provides a nucleic acid which codes for a lipase, e.g. any described above. This disclosure further provides a vector including such a nucleic acid. This disclosure also provides a non-human host cell including a nucleic acid, such as that described above. This disclosure also provides a method for preparing a lipase including cultivating a non-human host cell and isolating the lipase from the non-human host cell. Moreover, the disclosure provides a washing or cleaning agent including at least one lipase, e.g. any described above. The disclosure also provides a method for cleaning textiles or hard surfaces including the step of utilizing a washing or cleaning agent. This disclosure also provides a method of removing lipid stains or reducing odors in textiles including the step of utilizing a lipase, e.g. any described above. This disclosure also provides a nucleic acid which codes for a lipase, a non-human host cell including a vector, a non-human host cell including a lipase, a non-human host cell including a lipase obtained using any of the aforementioned methods, and a non-human host cell including a lipase obtained using one of the aforementioned methods and which secretes the lipase into a medium surrounding the host cell.

Surprisingly, it has now been found that a lipase from *Thermomyces lanuginosus* or a reasonably similar lipase (in terms of sequence identity) which has at least one amino-acid substitution at position 83, 86, 87, 89, 90, 92, 93, 95, 113, 174, 202, 203, 205, 206, 207, 208, 209, 211, 227, 252, 253, 256, 258, 259, 260, 264, or 267, in each case based on the numbering according to SEQ ID NO:1, is particularly suitable for use in washing or cleaning agents and causes reduced odor emissions, in particular on textiles which contain cotton and elastane.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Therefore, in a first aspect, the present disclosure relates to a lipase having an amino-acid sequence which is at least 70% identical to the amino-acid sequence shown in SEQ ID NO:1 over the entire length thereof, and having at least one amino-acid substitution at position 83, 86, 87, 89, 90, 92, 93, 95, 113, 174, 202, 203, 205, 206, 207, 208, 209, 211, 227, 252, 253, 256, 258, 259, 260, 264, or 267, in each case based on the numbering according to SEQ ID NO:1.

The present disclosure further relates to a method for preparing a lipase, comprising substituting at least one amino acid at at least one position which corresponds to positions 83, 86, 87, 89, 90, 92, 93, 95, 113, 174, 202, 203, 205, 206, 207, 208, 209, 211, 227, 252, 253, 256, 258, 259, 260, 264, or 267 in SEQ ID NO:1 in a starting lipase of which the sequence is at least 70% identical to the amino-acid sequence shown in SEQ ID NO:1 over the entire length thereof, preferably such that the lipase has at least one of the amino acid substitutions P208N. F211N, and P253N at at least one position.

A "lipase" within the meaning of the present patent application therefore covers both the lipase as such and a lipase prepared using a method according to the present disclosure as contemplated herein. All comments made with regard to the lipase therefore relate to both the lipase as a substance and the corresponding methods, in particular methods for preparing the lipase.

The present disclosure further relates to the lipases according to the present disclosure as contemplated herein, to the preparation method for lipases according to the present disclosure as contemplated herein, to nucleic acids which code for these lipases, to non-human host cells which contain lipases or nucleic acids according to the present disclosure as contemplated herein, to agents, in particular washing and cleaning agents, which comprise lipases according to the present disclosure as contemplated herein, to washing and cleaning methods, and to uses of the defined lipases according to the present disclosure as contemplated herein.

The present disclosure is based on the surprising finding that an alteration according to the present disclosure as contemplated herein at at least one of the positions 83, 86, 87, 89, 90, 92, 93, 95, 113, 174, 202, 203, 205, 206, 207, 208, 209, 211, 227, 252, 253, 256, 258, 259, 260, 264, or 267 of the lipase from *Thermomyces lanuginosus* according to SEQ ID NO:1 in a lipase of which the amino-acid sequence is at least 700/0 identical to the amino-acid sequence shown in SEQ ID NO. 1, such that another amino acid is present at at least one of the corresponding positions, causes minimized odor emissions, in particular on textiles which contain cotton and elastane. This is particularly surprising since the aforementioned amino-acid substitutions have not previously been associated with reduced odor emissions of the lipase. Particularly advantageous effects have been found for those lipases which have substitutions at the positions 208, 211, or 253, in particular 208N, 211N, or 253N.

The lipases according to the present disclosure as contemplated herein cause reduced odor emissions on textiles after the washing process, for example after textiles that contain cotton and elastane have been washed. This advantage is independent of the surfactants and/or bleaching agents used, the washing temperatures used, acidic or alkaline conditions, the pH conditions used, denaturing or oxidizing agents, and a change in redox behaviors. Particularly preferred embodiments of the present disclosure therefore provide lipase variants that are improved in terms of performance. Advantageous embodiments of this kind of lipases according to the present disclosure as contemplated herein therefore allow improved washing results on lipolytic-sensitive stains and reduced odor emissions after the washing process.

With respect to German patent application DE 102012224038 A1 and international patent application WO 2014/152674, mentioned at the outset, the present disclosure therefore relates to an alternative sequence alteration which leads to a reduction in odor emission after washing. This is surprising, as the substitution of at least one amino acid at position 83, 86, 87, 89, 90, 92, 93, 95, 113, 174, 202, 203, 205, 206, 207, 208, 209, 211, 227, 252, 253, 256, 258, 259, 260, 264, or 267, in each case based on the numbering according to SEQ ID NO:1, has not previously been associated with reduced odor emissions of the lipase.

A lipase according to the present disclosure as contemplated herein has enzymatic activity, i.e. it is capable of hydrolyzing fats and oils, in particular in a washing or cleaning agent. A lipase according to the present disclosure as contemplated herein is therefore an enzyme which catalyzes the hydrolysis of ester bonds in lipid substrates and is therefore capable of cleaving fats or oils. Furthermore, a lipase according to the present disclosure as contemplated herein is preferably a mature lipase, i.e. the catalytically active molecule without signal peptide(s) and/or propeptide(s). Unless indicated otherwise, the specified sequences also each relate to mature (processed) enzymes. In various embodiments, the lipase according to the present disclosure as contemplated herein contains at least one amino-acid substitution, which is selected from the group including of P208N, F211N, and P253N, in each case based on the numbering according to SEQ ID NO:1. In other preferred embodiments, the lipase according to the present disclosure as contemplated herein contains at least two or all three of the amino-acid substitutions P208N. F211N, and P253N, the numbering being in each case based on the numbering according to SEQ ID NO:1.

In various embodiments, the lipase according to the present disclosure as contemplated herein also has the amino-acid substitutions T231R and N233R, in each case based on the numbering according to SEQ ID NO:1. These substitutions are known in the prior art and are also contained, for example, in the lipase Lipex Evity 100 T which is already commercially obtainable.

In a further embodiment of the present disclosure, the lipase has an amino-acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.500, and 98.8% identical to the amino-acid sequence shown in SEQ ID NO:1 over the entire length thereof, and has an amino acid substitution, preferably the amino acids 208N, 211N, or 253N, at at least one of the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, preferably 208, 211, or 253, in the numbering according to SEQ ID NO:1. In the context of the present disclosure, the feature whereby a lipase has the stated substitutions means that it contains at least one non-native amino acid at one of the corresponding positions, preferably one of those explicitly mentioned, i.e. not all of the mentioned positions are otherwise mutated or deleted, for example by fragmentation of the lipase. Lipases of this kind, which are preferable according to the present disclosure as contemplated herein, are specified in SEQ ID NOs: 3-5.

The identity of nucleic-acid or amino-acid sequences is determined by a sequence comparison. This sequence comparison is based on the BLAST algorithm (cf. for example Altschul, S. F., Gish, W., Miller, W, Myers, E. W. & Lipman, D. J. (1990) "Basic local alignment search tool." J Mol. Biol. 215:403-410 and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pages 3389-3402) which is established and commonly used in the prior art and is carried out, in principle, by a similar series of nucleotides or amino acids in the nucleic-acid or amino-acid sequences being assigned to one another. The assignment of the relevant positions shown in a table is referred to as an "alignment". Another algorithm available from the prior art is the FASTA algorithm. Sequence comparisons (alignments), in particular multiple sequence comparisons, are generated using computer programs. For example, the Clustal series (cf. for example Chenna et al. (2003): Multiple sequence alignment with the Clustal series of programs. Nucleic Acid Research 31, 3497-3500), T-Coffee (cf. for example Notredame et al (2000): T-Coffee: A novel method for multiple sequence alignments. J. Mol. Biol. 302, 205-217) or programs based on these programs or algorithms are often used. Sequence comparisons (alignments) using the computer program Vector NTI® Suite 10.3 (Invitrogen Corporation, 1600 Faraday Avenue, Carlsbad, Calif., USA) with the specified standard parameters, the AlignX-Modul of which program for the sequence comparisons is based on ClustalW, are also possible.

A comparison of this kind makes it possible to confirm the similarity between the compared sequences. This similarity is usually expressed in percent identity, i.e. the percentage of identical nucleotides or amino-acid residues at the same positions or at positions that correspond to one another in an alignment. In amino-acid sequences, the broader concept of "homology" factors in conserved amino-acid exchanges, i.e. amino acids having similar chemical activity, since these usually have similar chemical activities within the protein. Therefore, the similarity between the compared sequences can also be expressed in percent homology or percent similarity. Information relating to identity and/or homology may apply to the entirety of the polypeptides or genes or only to individual segments. Homologous or identical segments of different nucleic-acid or amino-acid sequences are therefore defined by matches in the sequences. Segments of this kind often have identical functions. Said segments may be small and only comprise a few nucleotides or amino acids Segments that are this small often perform functions that are essential to the overall activity of the protein. Therefore, it may be expedient for sequence matches to only relate to individual, optionally small, segments. However, unless indicated otherwise, information relating to identity or homology in the present application relates to the entire length of the nucleic-acid or amino-acid sequence specified in each case.

In the context of the present disclosure, if it is stated that an amino-acid position corresponds to a numerically identified position in SEQ ID NO:1, this means that the corresponding position is assigned to the numerically identified position in SEQ ID NO:1 in an alignment as defined above.

In a further embodiment of the present disclosure, the lipase is exemplified wherein its cleaning performance is not significantly reduced by comparison with a lipase which has an amino-acid sequence that corresponds to the amino-acid sequence shown in SEQ ID NOs:1-5, i.e. said lipase has at least about 80%, of the reference washing performance. The cleaning performance can be determined in a washing system which contains a washing agent in a dosage of between about 4.5 and about 7.0 grams per liter of washing liquor, and the lipase, the lipase to be compared being used in the same concentration (based on the active protein) and the cleaning performance with respect to a stain on cotton is determined by measuring the extent to which the washed textiles have been cleaned. For example, the washing process can be carried out for about 70 minutes at a temperature of about 40° C., and the water can have a water hardness of between about 15.5 and about 16.5° (German degree of hardness). The concentration of the lipase in the washing agent intended for this washing system is from about 0.001 to about 0.1 wt. %, preferably from about 0.01 to about 0.06 wt. %, based on the purified active protein.

A preferred liquid washing agent for a washing system of this kind is composed as follows (all amounts are given in percent by weight): about 7% of alkyl benzene sulfonic acid, about 9% of anionic surfactants, about 4% of C12-C18 Na salts of fatty acids, about 7% of non-ionic surfactants, about 0.7% of phosphonates, about 3.2% of citric acid, about 3.0% of NaOH, about 0.04% of defoamer, about 5.7% of 1,2-propanediol, about 0.1% of preservatives, about 2% of ethanol, about 0.2% of dye-transfer-inhibitors, and the remaining percentage of demineralized water. The dosage of the liquid washing agent is preferably between about 4.5 and about 6.0 grams per liter of washing liquor, for example about 4.7, 4.9, or 5.9 grams per liter of washing liquor. Washing is preferably carried out within a pH range of between about pH 8 and about pH 10.5, preferably between about pH 8 and about pH 9.

Within the scope of the present disclosure, the cleaning performance is determined at about 40° C. using a liquid washing agent as specified above, the washing process preferably being carried out for about 30 minutes.

The degree of whiteness, i.e. the lightening of the stains, is determined using optical measurement methods, preferably photometrically, as a measure of cleaning performance A device suitable for this purpose is the spectrometer Minolta CM508d, for example. The devices used for the measurement are usually calibrated, in advance, against a white standard, preferably a white standard that is supplied therewith.

Each lipase being applied in an identical manner in terms of activity ensures that the relevant enzymatic properties, i.e. for example cleaning performance on particular stains, are compared even if there is some kind of divergence in the ratio of active substance to overall protein (the values for specific activity). In general, low specific activity can be compensated for by adding a larger amount of protein.

The lipase activity is determined in a manner that is routine in the art, specifically preferably as described in Bruno Stellmach, "Bestimmungsmethoden Enzyme für Pharmazie, Lebensmittelchemie, Technik, Biochemie, Biologie, Medizin" (Steinkopff Verlag Darmstadt, 1988, page 172ff). In this case, lipase-comprising samples are added to an olive oil emulsion in water comprising emulsifiers and incubated at about 30° C. and at about pH 9.0. In so doing, fatty acids are released. These are titrated using an autotitrator for about 20 minutes continuously using about 0.01 N sodium hydroxide solution, such that the pH remains constant ("pH-stat titration"). On the basis of the sodium hydroxide solution consumption, the lipase activity is determined by reference to a reference lipase sample.

An alternative test for establishing the lipolytic activity of the lipases according to the present disclosure as contemplated herein is an optical measurement method, preferably a photometric method. The test suitable for this purpose comprises the lipase-dependent cleavage of the substrate para-nitrophenyl butyrate (pNP butyrate). Said substrate is cleaved by the lipase into para-nitrophenolate and butyrate. The presence of para-nitrophenolate can be determined using a photometer, e.g. the Tecan Sunrise Device and XFLUOR software, at 405 nm, and it is thus possible to draw a conclusion on the enzymatic activity of the lipase.

In various embodiments, the lipase according to the present disclosure as contemplated herein has significantly reduced odor emissions by comparison with a lipase according to SEQ ID NO:1 and/or a lipase according to SEQ ID NO:2. In this context, "significantly" means that the lipase according to the present disclosure as contemplated herein has at most about 10%, 20%, 30%, 40%, 50%, 60%, 70%, 75%, 80%, 85%, 90%, 95% or 981% of the odor intensity which is determined for a lipase according to SEQ ID NO:1 and/or a lipase according to SEQ ID NO:2 In one exemplary method for determining the odor intensity caused by lipases, sheets made of textiles (these sheets may comprise, as required, various materials such as cotton, polyester, polyamides, viscose, Meryl, and elastane) are washed under the aforementioned conditions. The sheets are subsequently stored in airtight sample bottles until their odor intensity is determined by a testing panel—what is known as the sensory panel.

The protein concentration can be determined using known methods, for example the BCA method (bicinchoninic acid, 2,2'-biquinolyl-4,4'-dicarboxylic acid) or the Biuret method. (A. G. Gornall, C. S. Bardawill, and M. M. David, J. Biol. Chem., 177 (1948), pages 751-766). The active protein concentration can be determined, in this respect, by titrating the active centers using a suitable irreversible inhibitor and determining the residual activity (cf. M. Bender et al., J. Am. Chem. Soc. 88, 24 (1966), pages 5890-5913).

Proteins can be combined to form groups of immunologically related proteins by the reaction with an antiserum or a particular antibody. Those which belong to a group of this kind are exemplified wherein they have the same antigenic determinants which are detected by an antibody. They are therefore structurally so similar to one another that they are detected by an antiserum or particular antibodies. A further subject of the present disclosure is therefore lipases which are exemplified wherein they have at least one and, in order of increasing preference, two, three, or four antigenic determinants which match a lipase according to the present disclosure as contemplated herein. Lipases of this kind are structurally so similar to the lipase according to the present disclosure as contemplated herein as a result of their immunological matches that a similar function can also be assumed.

In addition to the aforementioned amino-acid alterations, lipases according to the present disclosure as contemplated herein can have further amino-acid alterations, in particular amino-acid substitutions, insertions, or deletions. Lipases of this kind are developed, for example, by targeted genetic alteration, i.e. by mutagenesis methods, and optimized for particular uses or in respect of specific properties (for example in respect of their catalytic activity, stability, etc.). Furthermore, nucleic acids according to the present disclosure as contemplated herein can be incorporated in recombination approaches and are thus used to produce completely new types of lipases or other polypeptides.

The aim is to introduce targeted mutations, such as substitutions, insertions, or deletions, into known molecules, in order to improve the cleaning performance of enzymes according to the present disclosure as contemplated herein, for example. For this purpose, in particular the surface charges and/or isoelectric point of the molecules, and thus their interactions with the substrate, can be altered. For example, the net charge of the enzymes can be changed in order to thereby influence the substrate binding, in particular for use in washing and cleaning agents. Alternatively or in addition, the stability of the lipase can be increased further still, and thus the cleaning performance thereof can be improved, by one or more appropriate mutations. Advantageous properties of individual mutations, e.g. individual substitutions, may complement one another. A lipase that has already been optimized in terms of particular properties, for example in terms of the stability thereof with respect to surfactants and/or bleaching agents and/or other components, can therefore also be developed within the scope of the present disclosure.

In order to describe substitutions that affect exactly one amino-acid position (amino-acid exchanges), the following convention is used: the internationally conventional single-letter code of the naturally present amino acid is given first, and then the associated sequence position, and finally the amino acid that has been added Several exchanges within the same polypeptide chain are separated from one another by slashes. For insertions, additional amino acids are indicated after the sequence position. For deletions, the amino acid that has been removed is replaced with a symbol, for example a star or a dash, or a Δ is put before the corresponding position. For example, P208N denotes the substitution of proline at position 95 by asparagine. P208PA denotes the insertion of alanine after the amino acid proline at position 208, and P208*, or ΔP208 denotes the deletion of proline from position 208. This nomenclature is known to a person skilled in the art of enzyme technology. Therefore, the present disclosure further relates to a lipase which is exemplified wherein it can be obtained from a lipase as described above acting as a starting molecule by one or more conservative amino-acid substitutions, the lipase still having in the numbering according to SEQ ID NO:1 at least one of the amino-acid substitutions according to the present disclosure as contemplated herein at the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, preferably 208, 211, or 253, in SEQ ID NO:1, as described above. The term "conservative amino-acid substitutions" means the exchange (substitution) of an amino-acid residue with another amino-acid residue, this exchange not resulting in a change in the polarity or charge at the position of the exchanged amino acid, e.g. the exchange of a nonpolar amino-acid residue with another nonpolar amino-acid residue. Within the scope of the present disclosure, conservative amino-acid substitutions include for example: G=A=S, I=V=L=M, D=E, N=Q, K=R, Y=F, S=T, G=A=I=V=L=M=Y=F=W=P=S=T.

Alternatively or in addition, the lipase is exemplified wherein it can be obtained from a lipase according to the present disclosure as contemplated herein acting as a starting molecule by fragmentation, deletion, insertion, or substitution mutagenesis and has an amino-acid sequence which matches that of the starting molecule over a length of at least 190, 200, 210, 220, 230, 240, 250, 260, or 269 interconnected amino acids, the at least one mutated amino-acid residue contained in the starting molecule still being present at the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, preferably 208, 211, or 253, in SEQ ID NO:1.

It is thus possible, for example, for individual amino acids to be deleted from tie enzyme termini or loops, without this resulting in the lipolytic activity being lost or reduced. Furthermore, by fragmentation, deletion, insertion, or substitution mutagenesis of this kind, the allergenicity of relevant enzymes, for example, can also be reduced and thus the usability thereof can be improved overall. The enzymes advantageously still have their lipolytic activity even after the mutagenesis, i.e. the lipolytic activity thereof corresponds at least to that of the starting enzyme, i.e. in a preferred embodiment, the lipolytic activity is at least about 80%, preferably at least about 90%, of the activity of the starting enzyme. Other substitutions can also have advantageous effects. It is possible to exchange a single amino acid or several interconnected amino acids with other amino acids.

Alternatively or additionally, the lipase is exemplified wherein it can be obtained from a lipase according to the present disclosure as contemplated herein acting as a starting molecule by one or more conservative amino-acid substitutions, the lipase having at least one of the amino-acid substitutions at the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, according to SEQ ID NO:1, preferably at least one of the substitutions P208N, F211N, or P253N.

In further embodiments, the lipase is exemplified wherein it can be obtained from a lipase according to the present disclosure as contemplated herein acting as a starting molecule by fragmentation, deletion, insertion, or substitution mutagenesis and has an amino-acid sequence which matches that of the starting molecule over a length of at least 190, 200, 210, 220, 230, 240, 250, 260, or 269 interconnected amino acids, the lipase comprising at least one of the amino-acid substitutions at the positions which correspond to positions 83, 86, 87, 89, 90, 92, 93, 95, 113, 174, 202, 203, 205, 206, 207, 208, 209, 211, 227, 252, 253, 256, 258, 259, 260, 264, or 267, according to SEQ ID NO:1, preferably at least one of the substitutions P208N, F211N, or P253N.

In this case, the other amino-acid positions are defined by an alignment of the amino-acid sequence of a lipase according to the present disclosure as contemplated herein with the amino-acid sequence of the lipase from *Thermomyces lanuginosus*, as shown in SEQ ID NO:1. Furthermore, the assignment of the positions is determined by the mature protein. In particular, this assignment is also used if the amino-acid sequence of a lipase according to the present disclosure as contemplated herein has a higher number of amino-acid residues than the lipase from *Thermomyces lanuginosus* according to SEQ ID NO:1. Proceeding from the mentioned positions in the amino-acid sequence of the lipase from *Thermomyces lanuginosus*, the alteration positions in a lipase according to the present disclosure as contemplated herein are those which are precisely assigned to these positions in an alignment.

Advantageous positions for sequence alterations, in particular substitutions, of the lipase from *Thermomyces lanuginosus* which when transferred to homologous positions of the lipases according to the present disclosure as contemplated herein are preferably of significance and impart advantageous functional properties to the lipase are therefore positions 83, 86, 87, 89, 90, 92, 93, 95, 113, 174, 202, 203, 205, 206, 207, 208, 209, 211, 227, 252, 253, 256, 258, 259, 260, 264, or 267, for assignment in an alignment with SEQ ID NO:1 and thus in the numbering according to SEQ ID NO:1. The following amino-acid residues are present in the stated positions in the wild-type molecule of the lipase from *Thermomyces lanuginosus*: S83, I86, E87, W89, I90, N92, L93, F95, F113, P174, I202, V203, R205, L206, P207, P208, R209, F211, L227, I252, P253, P256, H258, L259, W260, L264, and T267. Further confirmation of the correct assignment of the amino acids to be altered, i.e. in particular of the functional correspondence thereof, can be provided by comparison tests during which the two positions assigned to one another on the basis of an alignment are altered in the same way in the two lipases being compared with one another and it is observed whether the enzymatic activity is altered in the same way in the two lipases. If, for example, an amino-acid exchange at a particular position of the lipase from *Thermomyces lanuginosus* according to SEQ ID NO:1 is associated with a change in an enzymatic parameter, for example with the increase in the $K_M$ value, and if a corresponding change in the enzymatic parameter, thus for example also an increase in the $K_M$ value, is observed in a lipase variant according to the present disclosure as contemplated herein of which the amino-acid exchange was achieved by the same added amino acid, this is considered to be confirmation of the correct assignment.

All elements specified can also be applied to the methods according to the present disclosure as contemplated herein for preparing a lipase. A method according to the present disclosure as contemplated herein therefore further comprises one or more of the following method steps:

a) introducing one or more conservative amino-acid substitutions, the lipase having at least one amino-acid substitution at the positions which correspond to positions 83, 86, 87, 89, 90, 92, 93, 95, 113, 174, 202, 203, 205, 206, 207, 208, 209, 211, 227, 252, 253, 256, 258, 259, 260, 264, and 267 according to SEQ ID NO:1, preferably P208N, F211N, or P253N;

b) altering the amino-acid sequence by fragmentation, deletion, insertion, or substitution mutagenesis such that the lipase has an amino-acid sequence which matches that of the starting molecule over a length of at least 190, 200, 210, 220, 230, 240, 250, 260, or 269 interconnected amino acids, the lipase having at least one amino-acid substitution at the positions which correspond to positions 83, 86, 87, 89, 90, 92, 93, 95, 113, 174, 202, 203, 205, 206, 207, 208, 209, 211, 227, 252, 253, 256, 258, 259, 260, 264, and 267 according to SEQ ID NO:1, preferably P208N, F211N, or P253N.

In various embodiments of the preparation method, the lipase according to the present disclosure as contemplated herein also comprises the amino-acid substitutions T231R and/or N233R, in each case based on the numbering according to SEQ ID NO:1. These substitutions are preferably both present and combined with at least one of the substitutions disclosed herein.

All comments made above in relation to the lipases also apply to the methods according to the present disclosure as contemplated herein.

In further embodiments of the present disclosure, the lipase according to the present disclosure as contemplated herein or the lipase prepared using a method according to present disclosure as contemplated herein is still at least about 700%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to the amino-acid sequence shown in SEQ ID NO:1 over the entire length thereof. Alternatively, the lipase according to the present disclosure as contemplated herein or the lipase prepared using a method according to the present disclosure as contemplated herein is still at least about 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, or 98% identical to the amino-acid sequence shown in SEQ ID NOs:2-5 over the entire length thereof. The lipase or the lipase prepared using the method according to the present disclosure as contemplated herein has at least one amino-acid substitution at the positions 83, 86, 87, 89, 90, 92, 93, 95, 113, 174, 202, 203, 205, 206, 207, 208, 209, 211, 227, 252, 253, 256, 258, 259, 260, 264, or 267, in each case based on the numbering according to SEQ ID NO. 1. In more preferred embodiments, the at least one amino-acid substitution is selected from the group including of 208N, 211N. and 253N, in each case based on the numbering according to SEQ ID NO:1 In further preferred embodiments, the lipase has the amino-acid substitutions P208N, F211N or P253N, or two or all three of these substitutions.

The present disclosure also relates to a lipase as described above which is additionally stabilized, in particular by one or more mutations, for example substitutions, or by being coupled to a polymer. Increasing stability during storage and/or during use, for example during the washing process, leads to the enzymatic activity being maintained for longer and thus to the cleaning performance being improved. In principle, all stabilizing possibilities that are expedient and/or described in the prior art can be considered for this. Stabilizations which are achieved by mutations of the enzyme itself are preferred, since stabilizations of this kind do not require any further working steps after the enzyme has been obtained. Examples of sequence alterations suitable for this purpose have been mentioned above. Further suitable sequence alterations are known from the prior art. Possibilities for stabilization include for example:
  protecting against the influence of denaturing agents, such as surfactants, by mutations which cause the amino-acid sequence to be altered on or at the surface of the protein,
  exchanging amino acids which are close to the N-terminus with amino acids which are assumed to come into contact with the rest of the molecule by non-covalent interactions, and thus contribute to maintaining the globular structure.

Preferred embodiments are those in which the enzyme is stabilized in several different ways, since several stabilizing mutations have a cumulative or synergistic effect.

The present disclosure also relates to a lipase as described above which is exemplified wherein it has at least one chemical modification. A lipase that is altered in this way is referred to as a "derivative", i.e. the lipase is derivatized. Within the meaning of the present application, "derivatives" are therefore understood to mean proteins of which the pure amino-acid chain has been modified chemically. Derivatizations of this kind can be carried out in vivo, for example, by the host cell which expresses the protein. In this respect, couplings to low-molecular-weight compounds, such as lipids or oligosaccharides, are of particular importance. However, derivatizations may also be carried out in vitro, for example by the chemical conversion of a side chain of an amino acid or by covalent bonding of another compound to the protein. For example, it is possible to couple amines to carboxyl groups of an enzyme in order to change the isoelectric point. This other compound may also be another protein which is bound to a protein according to the present disclosure as contemplated herein via bifunctional chemical compounds, for example Derivatization is also understood to mean covalent bonding to a macromolecular carrier, or non-covalent inclusion in suitable macromolecular cage structures Derivatizations can, for example, influence the substrate specificity or the bond strength to the substrate or cause temporary inhibition of enzymatic activity, if the coupled substance is an inhibitor. This can be expedient in terms of the period of storage, for example. Modifications of this kind can also influence stability or enzymatic activity. They can also be used to reduce the allergenicity and/or immunogenicity of the protein and to thus increase the skin compatibility thereof, for example. For example, couplings to macromolecular compounds, for example polyethylene glycol, can improve the protein in terms of stability and/or skin compatibility. In the broadest sense, derivatives of a protein according to the present disclosure as contemplated herein can be understood to also include preparations of these proteins. Depending on how a protein is obtained, recovered or prepared, said protein can be accompanied by a wide range of other substances, for example from the culture of the microorganisms that produce it. A protein may also have been deliberately mixed with other substances in order to increase its storage stability, for example. Therefore, the present disclosure also covers all preparations of a protein according to the present disclosure as contemplated herein. This is still true irrespective of whether or not this enzymatic activity actually develops in a particular preparation. This is because it may be desirable for the protein to not have any activity or to only have low activity when being stored, and for the enzymatic function to only develop once the protein is in use. This can be controlled, for example, by appropriate accompanying substances. In particular, in this respect, it is possible to jointly prepare lipases and specific inhibitors.

With regard to all above-described lipases or lipase variants and/or derivatives, within the scope of the present disclosure, lipases, lipase variants and/or derivatives of which the odor emissions correspond at least to that of the lipase according to SEQ ID NOs:3-5 are particularly preferred, the intensity of the odor emissions being determined in a method, as described above.

The present disclosure also relates to a nucleic acid which codes for a lipase according to the present disclosure as contemplated herein, and to a vector comprising a nucleic acid of this kind, in particular a cloning vector or an expression vector.

These may be DNA or RNA molecules. They may be present as a single strand, as a single strand that is complementary to the first single strand, or as a double strand. In the case of DNA molecules in particular, the sequences of the two complementary strands should be taken into account in all three possible reading frames. It should also be noted that different codons, i.e. base triplets, can code for the same amino acids, such that a particular amino-acid sequence can be coded for by several different nucleic acids. Owing to this degeneracy of the genetic code, all nucleic-acid sequences which can code for one of the above-described lipases are included in this subject of the present disclosure. A person skilled in the art is able to identify these nucleic-acid sequences with absolute certainty since, despite the degeneracy of the genetic code, defined amino acids can be assigned to individual codons. Therefore, proceeding from an amino-acid sequence, a person skilled in the art can easily identify nucleic acids which code for said amino-acid sequence. Furthermore, in nucleic acids according to the present disclosure as contemplated herein, one or more codons can be replaced by synonymous codons. This aspect relates in particular to the heterologous expression of the enzymes according to the present disclosure as contemplated herein Therefore, each organism, for example a host cell of a production strain, has a particular codon usage "Codon usage" is understood to mean the translation of the genetic code into amino acids by the relevant organism. Bottlenecks can occur in protein biosynthesis if the codons on the nucleic acid are accompanied by a comparatively low number of charged tRNA molecules in the organism. Although coding for the same amino acid, this leads to a codon being translated less efficiently in the organism than a synonymous codon which codes for the same amino acid. Owing to the presence of a higher number of tRNA molecules for the synonymous codon, said codon can be translated more efficiently in the organism.

Using methods which are currently generally known, such as chemical synthesis or polymerase chain reaction (PCR), in conjunction with standard methods in molecular biology and/or protein chemistry, it is possible for a person skilled in the art, on the basis of known DNA and/or amino-acid sequences, to produce the corresponding nucleic acids and even complete genes Methods of this kind are known from, for example, Sambrook, J, Fritsch, E. F., and Maniatis, T. 2001. Molecular cloning: a laboratory manual, 3rd Edition Cold Spring Laboratory Press.

Within the meaning of the present disclosure, vectors are understood to mean elements which consist of nucleic acids and which contain a nucleic acid according to the present disclosure as contemplated herein as an exemplary nucleic-acid range. Vectors allow establishment of this nucleic acid in a species or a cell line over multiple generations or cell divisions as a stable genetic element. Vectors are specific plasmids, i.e. circular genetic elements, in particular for use in bacteria. Within the scope of the present disclosure, a nucleic acid according to the present disclosure as contemplated herein is cloned in a vector. These may include vectors, for example, which originate from bacterial plasmids, from viruses, or from bacteriophages, or predominantly synthetic vectors or plasmids having elements of various origins. Using the further genetic elements which are present in each case, vectors are able to become established as stable units in the host cells in question over several generations They may be present as separate units outside of a chromosome or be integrated in a chromosome or chromosomal DNA.

Expression vectors have nucleic-acid sequences which enable them to replicate in the host cells, preferably microorganisms, particularly preferably bacteria, which contain them and to express therein a contained nucleic acid. The expression is influenced, in particular, by promoter(s) which regulate the transcription. In principle, the expression can be carried out by the natural promoter which is originally located in front of the nucleic acid to be expressed, by a promoter of the host cell provided on the expression vector, or by a modified or completely different promoter of another organism or another host cell. In the present case, at least one promoter is provided for the expression of a nucleic acid according to the present disclosure as contemplated herein and is used for the expression thereof. Expression vectors can also be regulated, for example by changing the culturing conditions, by reaching a particular cell density in the host cells comprising said vectors, or by adding particular substances, in particular activators for gene expression. An example of a substance of this kind is the galactose derivative isopropyl-β-D-thiogalactopyranoside (IPTG) which is used as an activator for the bacterial lactose operon (lac operon). Unlike in expression vectors, the contained nucleic acid in cloning vectors is not expressed.

The present disclosure also relates to a non-human host cell comprising a nucleic acid according to the present disclosure as contemplated herein or a vector according to the present disclosure as contemplated herein, or comprising a lipase according to the present disclosure as contemplated herein, in particular a non-human host cell which secretes the lipase into the medium surrounding the host cell A nucleic acid according to the present disclosure as contemplated herein or a vector according to the present disclosure as contemplated herein is preferably transformed into a microorganism which then constitutes a host cell according to the present disclosure as contemplated herein. Alternatively, individual components, i.e. nucleic-acid parts or fragments of a nucleic acid according to the present disclosure as contemplated herein, can be introduced into a host cell such that the resulting host cell contains a nucleic acid according to the present disclosure as contemplated herein or a vector according to the present disclosure as contemplated herein. This procedure is particularly suitable if the host cell already contains one or more components of a nucleic acid according to the present disclosure as contemplated herein or of a vector according to the present disclosure as contemplated herein, and the additional components are then added accordingly. Methods for transforming cells are established in the prior art and are sufficiently known to a person skilled in the art. In principle, all cells, i.e. prokaryotic or eukaryotic cells, are suitable as host cells. Preferred host cells are those which may be advantageously managed genetically, which involves, for example, transformation using the nucleic acid or the vector and stable establishment thereof, for example unicellular fungi or bacteria. In addition, preferred host cells are distinguished by good microbiological and biotechnological manageability. This relates, for example, to ease of culturing, high growth rates, low demands on fermentation media, and good production and secretion rates for foreign proteins. Preferred host cells according to the present disclosure as contemplated herein secrete the (transgenically) expressed protein into the medium surrounding the host cells. Furthermore, the lipases can be modified, following preparation, by the cells that produced them, for example by the attachment of sugar molecules, by formylations, by aminations, etc. Post-translational modifications of this kind can influence the lipase in terms of its function.

Those host cells of which the activity can be regulated due to genetic regulation elements which are provided on the vector, for example, but which may also be present in these cells from the outset, represent other preferred embodiments. These host cells may be induced to express, for example by the controlled addition of chemical compounds which are used as activators, by changing the culturing conditions, or upon reaching a particular cell density. This provides for cost-effective production of the proteins according to the present disclosure as contemplated herein. An example of a compound of this kind is IPTG, as described above.

Prokaryotic or bacterial cells are preferred host cells. Bacteria are distinguished by short generation times and low demands on the culturing conditions. Cost-effective culturing methods or preparation methods can thereby be established. Furthermore, a person skilled in the art has a vast pool of experience with regard to bacteria in fermentation technology. Gram-negative or gram-positive bacteria may be suitable for specific production for a wide variety of reasons, which should be determined by experiment in any given case, for example nutrient sources, product formation rate, time constraints, etc.

In the case of gram-negative bacteria, such as *Escherichia coli*, numerous proteins are secreted into the periplasmatic space, i.e. the compartment between the two membranes which enclose the cells. This may be advantageous for specific applications. Furthermore, gram-negative bacteria may also be formed such that they secrete the expressed proteins not only into the periplasmatic space, but also into the medium surrounding the bacterium By contrast, gram-positive bacteria, for example Bacilli or actinomycetes or other representatives of the actinomycetales, have no outer membrane, and therefore secreted proteins are released directly into the medium surrounding the bacteria, generally the nutrient medium, from which the expressed proteins may be purified. They may be isolated directly from the medium or processed further. Moreover, gram-positive bacteria are related to or identical to most origin organisms for industrially significant enzymes and they themselves usually form comparable enzymes, such that they have a similar codon usage and the protein synthesis apparatus thereof is naturally aligned accordingly.

Host cells according to the present disclosure as contemplated herein may be altered in terms of their requirements for culture conditions, may have different or additional selection markers, or may express different or additional proteins. These host cells may be in particular host cells that express a plurality of proteins or enzymes transgenically. The present disclosure can be used, in principle, for all microorganisms, in particular for all fermentable microorganisms, particularly preferably for those from the *Bacillus* genus, and leads to it being possible to prepare proteins according to the present disclosure as contemplated herein by using microorganisms of this kind. Microorganisms of this kind then constitute host cells within the meaning of the present disclosure.

In a further embodiment of the present disclosure, the host cell is exemplified wherein it is a bacterium, preferably a bacterium selected from the group of the genera of *Escherichia, Klebsiella, Bacillus, Staphylococcus, Corynebacterium, Arthrobacter, Streptomyces, Stenotrophomonas*, and *Pseudomonas*, more preferably a bacterium selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor*, and *Stenotrophomonas maltophilia*.

However, the host cell may also be a eukaryotic cell which is exemplified wherein it has a nucleus. Therefore, the present disclosure further relates to a host cell which is exemplified wherein it has a nucleus Unlike prokaryotic cells, eukaryotic cells are able to modify the formed protein post-translationally. Examples of eukaryotic cells are fungi such as actinomycetes or yeasts such as *Saccharomyces* or *Kluyveromyces*. This may be particularly advantageous, for example, if, in the context of their synthesis, the proteins are intended to undergo specific modifications which systems of this kind allow. The modifications which are carried out by eukaryotic systems, particularly in the context of protein synthesis, include, for example, the binding of low-molecular-weight compounds such as membrane anchors or oligosaccharides. Oligosaccharide modifications of this kind may be desirable, for example, as a way to reduce the allergenicity of an expressed protein. A co-expression with the enzymes formed naturally by cells of this kind, such as cellulases, can also be advantageous. Furthermore, thermophilic fungal expression systems, for example, may be particularly suitable for expressing temperature-resistant proteins or variants.

The host cells according to the present disclosure as contemplated herein are cultured and fermented in a conventional manner, for example in batch or continuous systems. In the first case, a suitable nutrient medium is inoculated with the host cells, and the product is harvested from the medium after a period of time that can be determined by experiment. Continuous fermentation is distinguished by the achievement of a steady state in which, over a comparatively long period of time, some cells die, but also regenerate, and at the same time, the formed protein can be removed from the medium.

Host cells according to the present disclosure as contemplated herein are preferably used in order to prepare lipases according to the present disclosure as contemplated herein. Therefore, the present disclosure also relates to a method for preparing a lipase, comprising.

a) culturing a host cell according to the present disclosure as contemplated herein, and b) isolating the lipase from the culture medium or from the host cell.

This subject of the present disclosure preferably includes fermentation methods. Fermentation methods are known per se from the prior art, and constitute the actual large-scale production step, generally followed by a suitable method for purifying the prepared product, for example the lipase according to the present disclosure as contemplated herein. All fermentation methods which are based on a corresponding method for preparing a lipase according to the present disclosure as contemplated herein constitute embodiments of this subject of the present disclosure.

Fermentation methods which are exemplified wherein the fermentation is carried out via an inflow strategy are in particular considered Here, the media components that are consumed by the continuous culturing are fed in. Significant increases both in the cell density and in the cell mass or dry mass, and/or in particular in the activity of the lipase of interest, can be achieved in this way. Furthermore, the fermentation may also be designed in such a way that undesirable metabolic products are filtered out, or neutralized by adding a buffer or appropriate counterions.

The prepared lipase can be harvested from the fermentation medium. A fermentation method of this kind is preferred over isolation of the lipase from the host cell, i.e. product recovery from the cell mass (dry mass), however, said method requires that suitable host cells or one or more suitable secretion markers or mechanisms and/or transport systems be provided, so that the host cells secrete the lipase into the fermentation medium. Alternatively, without secretion, the lipase can be isolated from the host cell, i.e. separated from the cell mass, for example by precipitation with ammonium sulfate or ethanol, or by chromatographic purification.

All aforementioned elements can be combined to form methods for preparing lipases according to the present disclosure as contemplated herein.

The present disclosure also relates to an agent which is exemplified wherein it contains a lipase according to the present disclosure as contemplated herein, as described above. The agent is preferably a washing or cleaning agent. This covers all conceivable types of washing or cleaning agents, including both concentrates and agents to be used in undiluted form, for use on a commercial scale, in washing machines, or for washing or cleaning by hand. These agents include, for example, washing agents for textiles, carpets, or natural fibers for which the term "washing agent" is used. These also include, for example, dishwashing detergents for dishwashers or manual dishwashing detergents or cleaners for hard surfaces, such as metal, glass, porcelain, ceramics, tiles, stone, coated surfaces, plastics materials, wood, or leather for which the term "cleaning agent" is used, i.e. in addition to manual and automatic dishwashing detergents, also abrasive cleaners, glass cleaners, WC rimblocks, etc. Within the scope of the present disclosure, the washing and cleaning agents also include auxiliary washing agents, which are added to the actual washing agent when washing textiles manually or using a machine in order to achieve an additional effect. Furthermore, within the scope of the present disclosure, washing and cleaning agents also include textile pre-treatment and post-treatment agents, i.e. agents with which the piece of laundry comes into contact before it is actually washed, for example in order to loosen stubborn dirt, and also agents which impart other desirable properties to the laundry, for example softness to touch, crease resistance, or low static charge, in a step that comes after the actual textile washing process. The agents mentioned last include, inter alia, softeners.

The washing or cleaning agents according to the present disclosure as contemplated herein, which may be present in the form of powdered solids, compressed particles, homogeneous solutions, or suspensions, can contain, in addition to a lipase according to the present disclosure as contemplated herein, all known ingredients that are common in agents of this kind, at least one further ingredient preferably being present in the agent.

The agents according to the present disclosure as contemplated herein may contain surfactants, builders, peroxygen compounds, or bleach activators, in particular. They may also contain water-miscible organic solvents, further enzymes, sequestering agents, electrolytes, pH regulators, and/or further auxiliaries such as optical brighteners, graying inhibitors, foam regulators, and dyes and fragrances, and combinations thereof.

In particular, a combination of a lipase according to the present disclosure as contemplated herein with one or more further ingredient(s) of the agent is advantageous, since an agent of this kind has improved cleaning performance in preferred embodiments according to the present disclosure as contemplated herein on account of synergies obtained thereby. In particular, such synergy can be achieved by the combination of a lipase according to the present disclosure as contemplated herein with a surfactant and/or a builder and/or a peroxygen compound and/or a bleach activator.

Advantageous ingredients of agents according to the present disclosure as contemplated herein are disclosed in international patent application WO2009/121725, starting on the penultimate paragraph of page 5 and ending on page 13 after the second paragraph. Reference is made explicitly to this disclosure and the content thereof is incorporated in the present patent application.

In other embodiments of the present disclosure, the agent is exemplified wherein it contains
(a) from about 1 to about 85 wt. %, preferably from about 5 to about 65 wt. %, of surfactants; and/or
(a) from about 0 to about 45 wt. %, preferably from about 0.1 to about 15 wt. %, of builders; and/or
(a) from about 0.0005 to about 15 wt. %, preferably from about 0.001 to about 5 wt. %, of protease; and/or
(a) from about 0.0005 to about 15 wt. %, preferably from about 0.001 to about 5 wt. %, of amylase; and/or
(a) from about 0.00005 to about 15 wt. %, preferably from about 0.0001 to about 5 wt. %, of mannanase; and/or
(a) from about 0.00005 to about 15 wt. %, preferably from about 0.0001 to about 5 wt %, of cellulase/pectate lyase; and/or
(a) from about 0.00005 to about 15 g/wash load, preferably from about 0.0001 to about 5 g/wash load, of xanthan lyase; and/or
(a) from about 0.00005 to about 15 g/wash load, preferably from about 0.00005 to about 15 g/wash load, of endoglucanase, which is capable of digesting xanthan.

An agent according to the present disclosure as contemplated herein advantageously contains the lipase in an amount of from about 2 μg to about 20 mg, preferably from about 5 μg to about 17.5 mg, particularly preferably from about 20 μg to about 15 mg, and very particularly preferably from about 50 μg to about 10 mg, per g of the agent. Furthermore, the agent according to the present disclosure as contemplated herein can advantageously contain the lipase in an amount of from about 0.00005 to about 15 wt. %, preferably from about 0.0001 to about 5 wt. %, and particularly preferably from about 0.001 to about 1 wt. %, based on the active enzyme. Furthermore, the lipase contained in the agent and/or further ingredients of the agent may be encapsulated in a substance that is impermeable to the enzyme at room temperature or in the absence of water, which substance becomes permeable to the enzyme under use conditions of the agent. Such an embodiment of the present disclosure is thus exemplified wherein the lipase is encapsulated in a substance that is impermeable to the lipase at room temperature or in the absence of water. Furthermore, the washing or cleaning agent itself can also be packaged in a container, preferably an airtight container, from which it is released shortly before use or during the washing process.

In other embodiments of the present disclosure, the agent is exemplified wherein it
(a) is present in solid form, in particular as a flowable powder having a bulk density of from about 300 g/l to about 1200 g/l, in particular from about 500 g/l to about 900 g/l, or
(b) is present in pasty or liquid form, and/or
(c) is present in gel or pouch form, and/or (d) is present as a single-component system, or
(e) is divided into a plurality of components.

These embodiments of the present disclosure cover all solid, powder, liquid, gel, or paste dosage forms of agents according to the present disclosure as contemplated herein that may optionally also consist of a plurality of phases, and may be present in compressed or uncompressed form. The agent may be present in the form of a flowable powder, in particular having a bulk density of from about 300 g/l to about 1200 g/l, more particularly from about 500 g/l to about 900 g/l or from about 600 g/l to about 850 g/l. The solid dosage forms of the agent also include extrudates, granules, tablets, or pouches. Alternatively, the agent may also be a liquid, gel, or paste, for example in the form of a non-aqueous liquid washing agent or a non-aqueous paste or in the form of an aqueous liquid washing agent or water-comprising paste. Furthermore, the agent may be present as a single-component system. Agents of this kind typically consist of one phase. Alternatively, an agent can also consist of a plurality of phases. An agent of this kind is therefore divided into a plurality of components.

Washing or cleaning agents according to the present disclosure as contemplated herein may only contain a lipase. Alternatively, they may also contain further hydrolytic enzymes or other enzymes in a concentration that is expedient in terms of the effectiveness of the agent. Another embodiment of the present disclosure thus relates to agents which also comprise one or more further enzymes. All enzymes which can develop catalytic activity in the agent according to the present disclosure as contemplated herein, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase, or other lipases that are different from the lipase according to the present disclosure as contemplated herein, and mixtures thereof, can preferably be used as further enzymes. Further enzymes are contained in the agent advantageously in an amount of from about 1×about $10^{-8}$ to about 5 wt. % in each case, based on the active protein. Each further enzyme is contained in agents according to the present disclosure as contemplated herein in an amount of, in order of increasing preference, from about $1 \times 10^{-7}$ to about 3 wt. %, from about 0.00001 to about 1 wt. %, from about 0.00005 to about 0.5 wt. %, from about 0.0001 to about 0.1 wt. %, and most particularly preferably from about 0.0001 to about 0.05 wt. %, based on the active protein. The enzymes particularly preferably have synergistic cleaning performances with respect to particular stains or marks, i.e. the enzymes contained in the agent composition assist one another in terms of the cleaning performance thereof. Very particularly preferably, such synergy exists between the lipase contained according to the present disclosure as contemplated herein and a further enzyme of an agent according to the present disclosure as contemplated herein, in particular between the stated lipase and an amylase and/or a protease and/or a mannanase and/or a cellulase and/or a pectinase. Synergistic effects can occur not only between different enzymes, but also between one or more enzymes and other ingredients of the agent according to the present disclosure as contemplated herein.

The present disclosure further relates to a method for cleaning textiles or hard surfaces, exemplified wherein an agent according to the present disclosure as contemplated herein is used in at least one method step, or in that a lipase according to the present disclosure as contemplated herein becomes catalytically active in at least one method step, in particular such that the lipase is used in an amount of from about 40 µg to about 4 g, preferably from about 50 µg to about 3 g, particularly preferably from about 100 µg to about 2 g, and very particularly preferably from about 200 µg to about 1 g.

In various embodiments, the above-described method is distinguished in that the lipase is used at a temperature of from about 0 to about 100° C., preferably from about 0 to about 60° C., more preferably from about 20 to about 45° C., and most preferably at a temperature of 40° C.

These embodiments include both manual and automatic methods, automatic methods being preferred. Methods for cleaning textiles are generally distinguished in that various substances that have a cleaning effect are applied to the item to be cleaned in a plurality of method steps and washed off after the contact time, or in that the item to be cleaned is treated with a washing agent or a solution or dilution of this agent in some other way. The same applies to methods for cleaning all materials other than textiles, in particular hard surfaces. All conceivable washing or cleaning methods can be enhanced in at least one of the method steps by the use of a washing or cleaning agent according to the present disclosure as contemplated herein or a lipase according to the present disclosure as contemplated herein, and then constitute embodiments of the present disclosure. All elements, subjects, and embodiments that are described for lipases according to the present disclosure as contemplated herein and agents that contain them can also be applied to this subject of the present disclosure. Therefore, at this juncture, reference is explicitly made to the disclosure at the corresponding point when it was indicated that this disclosure also applies to the above methods according to the present disclosure as contemplated herein. Since lipases according to the present disclosure as contemplated herein naturally already have hydrolytic activity and these also develop in media that otherwise have no cleaning force, such as in simple buffers, an individual and/or the only step of a method of this kind can consist, if desired, in bringing a lipase according to the present disclosure as contemplated herein into contact with the stain as the only component that has a cleaning effect, preferably in a buffer solution or in water. This constitutes a further embodiment of this subject of the present disclosure.

Methods for treating textile raw materials or for textile care in which a lipase according to the present disclosure as contemplated herein becomes active in at least one method step also constitute alternative embodiments of this subject of the present disclosure. Of such methods, methods for textile raw materials, fibers, or textiles having natural components are preferred.

All elements, subjects, and embodiments that are described for lipases according to the present disclosure as contemplated herein and agents that contain them can also be applied to this subject of the present disclosure. Therefore, at this juncture, reference is explicitly made to the disclosure at the corresponding point when it was indicated that this disclosure also applies to the above use according to the present disclosure as contemplated herein.

In a further aspect, the present disclosure relates to the use of a lipase according to the present disclosure as contemplated herein or of a lipase that can be obtained using a method according to the present disclosure as contemplated herein in a washing or cleaning agent for removing lipid-comprising stains.

The lipases described herein are particularly distinguished by less odor formation when used in washing agents for textiles. A corresponding use for reducing undesired odor formation on textiles that have been washed using lipase-comprising washing agents therefore also forms part of the present disclosure. The present disclosure therefore relates in particular to the use of a lipase as described herein in a washing or cleaning agent for reducing bad odors in textiles washed with said agent.

All elements, subjects, and embodiments that are described for lipases according to the present disclosure as contemplated herein and agents that contain them can also be applied to these subjects of the present disclosure.

EXAMPLES

Example 1: Washing Conditions and Odor Test Overview of the Mutations

| Variant | Sequence | | | SEQ ID NO: |
|---|---|---|---|---|
| Variant 1 (comparative example) | | | | 1 |
| Variant 2 (according to thepresent disclosure as contemplated herein) | P208N | T231R | N233R | 3 |
| Variant 2 (according to the present disclosure as contemplated herein) | F211N | T231R | N233R | 4 |
| Variant 3 (according to the present disclosure as contemplated herein) | P253N | T231R | N233R | 5 |

Liquid washing agent formulations (see Table 1).
One formulation contained the reference lipase having the amino-acid sequence according to SEQ ID NO:1, further formulations contained the lipase according to the present disclosure as contemplated herein having the sequence according to SEQ ID NOs:3-5.

For the odor test, a microtiter plate was prepared with clean textile strips (cotton, 10 mm) The washing agent solution and microtiter plate were preheated to 40° C. The textile strips were washed for 1 hour at 40° C. using a washing liquor that contains lipase. The washing agent was diluted to a concentration of 4.7 g/l in the washing liquor. The lipase concentration was 0.4%. As a reference, the washing matrix without lipase was used After washing, the textile strips were dried and then soiled with fat stains. The added fats were added in the following ratio:

Rama (margarine):butter:skin fat:olive oil:mineral oil in a ratio of 1:1:1:2:2. Next, the textile strips prepared with fat stains were stored separately in airtight sample containers for 7 days at room temperature. A testing panel of 6 people (sensory panel) were employed for the odor test, in order to smell the textile strips after 7 days and assess their odor intensity. If lipase is present on the textile, the fatty stains are degraded and produce a bad odor. The odor test includes assessment on a scale of from 1 to 5, lower values being advantageous in respect of the odor. The results are shown in Table 2.

TABLE 1

Washing agent formulations used

| Ingredient | V1 | E1 |
|---|---|---|
| LAS-Na | 10.6 | 10.6 |
| FA 7 EO | 3 | 3 |
| C16-18 Na soap | 1.2 | 1.2 |
| HEDP-Na$_4$ | 0.81 | 0.81 |
| Polyacrylate | 2.2 | 2.2 |
| Sodium silicate 2.1 | 5.7 | 5.7 |
| Sodium carbonate | 22 | 22 |
| Sodium percarbonate | 10 | 10 |
| TAED | 3 | 3 |
| Acyl hydrazone | — | 0.09 |
| Carboxymethyl cellulose | 2.5 | 2.5 |
| Defoamer | 0.046 | 0.046 |
| Protease/amylase/cellulase | 0.61 | 0.61 |
| Lipase | 0.005 | 0.005 |
| Optical brightener | 0.183 | 0.183 |
| Perfume | 0.3 | 0.3 |
| Sodium sulfate | up to 100 | up to 100 |

TABLE 2

Results from the odor test

| Sample | Cotton |
|---|---|
| Reference (washing agent matrix without lipase) | 0.5 |
| Washing agent matrix + reference lipase (SEQ ID NO: 2) | 1.8 |
| Washing agent matrix + lipase according to the present disclosure as contemplated herein (SEQ ID NO: 3) | 1.1 |
| Washing agent matrix + lipase according to the present disclosure as contemplated herein (SEQ ID NO: 4) | 0.9 |
| Washing agent matrix lipase according to the present disclosure as contemplated herein (SEQ ID NO: 5) | 1.3 |

The results show that the lipase variants according to the present disclosure as contemplated herein are distinguished by reduced formation of bad odors by comparison with the wild-type enzyme.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability or configuration of the various embodiments in any way Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A lipase having an amino-acid sequence which is at least 91% identical to the amino-acid sequence shown in SEQ ID NO:1 over the entire length thereof, and having at least one amino-acid substitution selected from the group consisting of 208N, 211N and 253N, in each case based on the numbering of SEQ ID NO:1.

2. The lipase of claim 1, wherein the lipase has the amino-acid substitution(s) P208N, F211N and/or P253N, in each case based on the numbering of SEQ ID NO:1.

3. A lipase,
(a) obtained from a starting lipase of claim 1 acting as a starting molecule through one or more conservative amino-acid substitutions, the lipase having at least one amino-acid substitution selected from the group consisting of 208N, 211N and 253N, in each case based on the numbering of SEQ ID NO:1; and/or
(b) obtained from a starting lipase of claim 1 acting as a starting molecule through fragmentation, deletion, insertion, or substitution mutagenesis and has an amino-acid sequence which matches that of the starting molecule over a length of at least 190 interconnected amino acids, the lipase having at least one amino-acid substitution selected from the group consisting of 208N, 211N and 253N, in each case based on the numbering of SEQ ID NO:1.

4. The lipase of claim 1, wherein the lipase also has the amino-acid substitutions T231R and N233R, in each case based on the numbering of SEQ ID NO:1.

5. A washing or cleaning agent comprising at least one lipase of claim 1.

6. A method for cleaning textiles or hard surfaces, comprising the step of utilizing the washing or cleaning agent of claim 5.

7. A method of removing lipid stains or reducing odors in textiles comprising the step of utilizing the lipase of claim 1.

* * * * *